United States Patent [19] [11] 4,252,720
Schellhammer et al. [45] Feb. 24, 1981

[54] PYRAZOLINE COMPOUNDS

[75] Inventors: Carl-Wolfgang Schellhammer, Bergisch-Gladbach; Bernhard Wehling, Cologne, both of Fed. Rep. of Germany

[73] Assignee: Bayer Aktiengesellschaft, Leverkusen, Fed. Rep. of Germany

[21] Appl. No.: 967,440

[22] Filed: Dec. 7, 1978

[30] Foreign Application Priority Data

Dec. 9, 1977 [DE] Fed. Rep. of Germany ....... 2755023

[51] Int. Cl.³ ............................................ C07D 231/06
[52] U.S. Cl. ............................. 260/239.65; 260/239.9
[58] Field of Search ......................... 260/239.65, 239.9; 548/379

[56] References Cited

U.S. PATENT DOCUMENTS

| 3,131,079 | 4/1964 | Wagner et al. | 260/239.9 |
| 3,865,816 | 2/1975 | Mengler | 260/239.9 |
| 3,925,367 | 12/1975 | Boehmke et al. | 260/239.9 |
| 4,071,466 | 1/1978 | Schroeder et al. | 260/239.9 |
| 4,183,853 | 1/1980 | Schroeder et al. | 260/239.65 |

Primary Examiner—Henry R. Jiles
Assistant Examiner—Natalia Harkaway
Attorney, Agent, or Firm—Sprung, Felfe, Horn, Lynch & Kramer

[57] ABSTRACT

Compounds of the formula

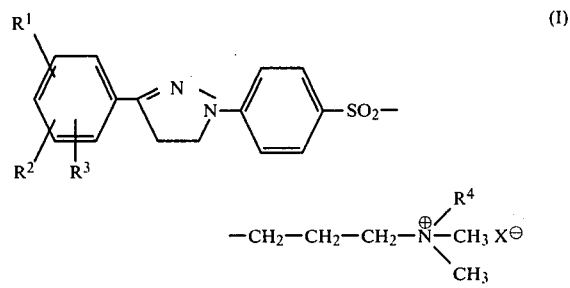

wherein
$R^1$, $R_2$ and $R_3$ denote hydrogen, chlorine or methyl,
$R^4$ denotes $C_1$-$C_4$-alkyl which is optionally substituted by phenyl, hydroxyl or $C_1$-$C_4$-alkoxy and
$X^\ominus$ denotes a colorless anion.

A process for their preparation and processes for brightening polyacrylonitrile and wool using compounds of the formula (I).

2 Claims, No Drawings

PYRAZOLINE COMPOUNDS

The invention relates to compounds of the formula

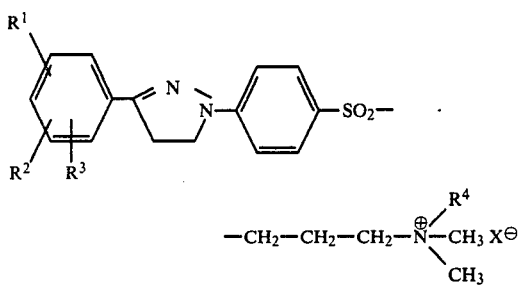

wherein
$R^1$, $R^2$ and $R^3$ denote hydrogen, chlorine or methyl,
$R^4$ denotes $C_1$-$C_4$-alkyl which is optionally substituted by phenyl, hydroxyl or $C_1$-$C_4$-alkoxy and
$X^\ominus$ denotes a colourless anion.

The pyrazoline compounds according to the invention can be prepared by reacting ketones of the formula

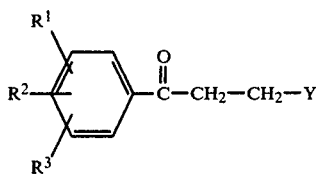

with the hydrazine of the formula

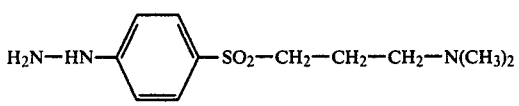

wherein
$R^1$, $R^2$ and $R^3$ have the abovementioned meaning and Y represents halogen, di-$C_1$-$C_4$-alkylamino, morpholino or piperidino,
the product being subsequently reacted with an alkylating agent.

Water-miscible solvents, such as alcohols, ethers and acids, in particular lower aliphatic alcohols, glycols and partial esters thereof, and ethers and acetic acid, are preferably employed during the condensation reaction.

Examples of suitable anions $X^-$ are halide ions, such as chloride, bromide or iodide, and sulphonate ions, such as methanesulphonate, ethanesulphonate, benzenesulphonate and toluenesulphonate.

Examples of alkylating agents which are accordingly used are methyl iodide, dimethyl sulphate, diethyl sulphate and p-toluenesulphonic acid methyl ester.

The hydrazine (III) is obtained by alkylating 4-chlorothiophenol with 1-chloro-3-dimethylaminopropane under alkaline catalysis, oxidising the thioether with hydrogen peroxide in a solution containing acetic acid and reacting the resulting 4-chlorophenyl 3-dimethylamino-propyl sulphone (IV) with hydrazine hydrate under reflux.

The compound (IV) can also be prepared by alkylating the sodium salt of 4-chlorophenylsulphinic acid with 1-chloro-3-dimethylaminopropane.

The compounds of the formula (I) are outstandingly suitable for whitening polyacrylonitrile and wool. Brightening effects with good fastness properties and a high degree of whiteness are obtained.

EXAMPLE 1

10 g of the compound of the formula

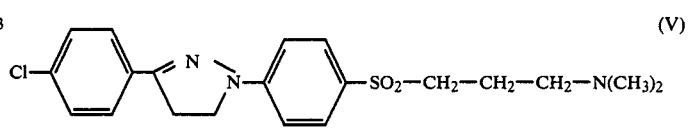

are dissolved in 300 ml of chlorobenzene at 50° C. A solution of 3.4 g of dimethyl sulphate in 30 ml of chlorobenzene is added dropwise in the course of 20 minutes and the mixture is stirred at 50° C. for 6 hours. 12.5 g of a compound of the formula

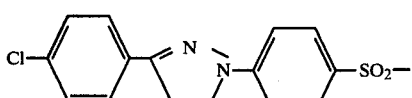
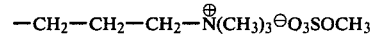

with a melting point of 226°–229° C. are isolated.

The free base (V) is prepared by the following route:
30 g of 4-chlorothiophenol are boiled under reflux with 24.4 g of 1-chloro-3-dimethylaminopropane and 8.4 g of sodium hydroxide in 800 ml of water and 200 ml of ethanol for 8 hours. The product is extracted with methylene chloride, the methylene chloride solution is dried, the solvent is stripped off and the product is distilled (boiling point: 110°–112° C. under 0.1 mm). 40 g of 4-chlorophenyl 3-dimethylaminopropyl thioether and 46 g of hydrogen peroxide (35% strength) in 300 ml of acetic acid are heated to 50° C. for 2 hours, then to 100° C. for 2 hours and finally to the reflux temperature for 5 hours. After distillation, 35 g of 4-chlorophenyl 3-dimethylaminopropyl sulphone, boiling point 170°–5° C. (0.2 mm), are obtained.

26 g of the 4-chlorophenyl 3-dimethylaminopropyl sulphone are heated under reflux with 78 g of hydrazine hydrate for 15 hours. After cooling, 23 g of 4-(3-dimethylaminopropylsulphonyl)-phenylhydrazine, which, when recrystallised from toluene, melts at 113°–5°C., precipitate.

10 g of 4-(3-dimethylaminopropylsulphonyl)-phenylhydrazine, 19.8 g of a 40% strength solution of 3-chloro-1-(4-chlorophenyl)-1-propanone in chlorobenzene and 4.6 g of concentrated hydrochloric acid are heated under reflux in 60 ml of methanol for 9 hours. The solvent is distilled off in vacuo, the residue is dissolved in 100 ml of water, the solution is rendered alkaline with sodium hydroxide solution and extracted with methylene chloride and the organic phase is evaporated in vacuo. After recrystallising the residue from methanol, 11 g of pyrazoline (V) of melting point 140°–142° C. are obtained.

The following quaternisation products can be obtained analogously: 1-[4-(3-ethyldimethylammonium)-propylsulphonylphenyl]-3-(4chlorophenyl)-pyrazoline ethyl-sulphate of melting point 190°–193° C.; 1-[4-(3-trimethylammonium)-propylsulphonylphenyl]-3-(4-chlorophenyl)-pyrazoline p-toluenesulphonate of melting point 193° C.; and 1-[4-(benzyldimethylammonium)-propylsulphonylphenyl]-3-(4-chlorophenyl)-pyrazoline chloride of melting point 226° C.

EXAMPLE 2

1-[p-(3-Dimethylamino-)-propylsulphonylphenyl]-3-(3,4-dichlorophenyl)-pyrazoline of melting point 165°–6° C. are obtained analogously to Example 1 by condensation of 4-(3-dimethylaminopropylsulphonyl)-phenylhydrazine with 3-chloro-1-(3,4-dichlorophenyl)-1-propanone.

The following compounds were obtained by quaternisation: 1-[4-(3-trimethylammonium)-propylsulphonyl-phenyl]-3(3,4-dichlorophenyl)-pyrazoline methosulphate of melting point 218°–219° C.; 1-[4-( b 3-ethyldimethylammonium)-propylsulphonylphenyl]-3-(3,4-dichlorophenyl)-pyrazoline ethyl-sulphate of melting point 194° C.; and 1-[4-(3-trimethylammonium)-propylsulphonylphenyl]-3-(3,4-dichlorophenyl) -pyrazoline p-toluene-sulphonate of melting point 193° C.

EXAMPLE 3

1-[4-(3-Dimethylamino)-propylsulphonylphenyl]-3-(4,5-dichloro-2-methylphenyl)-pyrazoline of melting point 144°–145° C. is obtained, as described in Example 1, by condensation of the hydrazine (III) with 3-chloro-1-(4,5-dichloro-2-methylphenyl)-1-propanone. Quaternisation led to the following compounds: 1-[4-(3-trimethylammonium)-propylsulphonylphenyl]-3-(4,5-dichloro-2-methylphenyl)-pyrazoline methosulphate of melting point 234° C.; 1-[4-(3-ethyldimethylammonium)-propylsulphonylphenyl]-3-(4,5-dichloro-2-methylphenyl)-pyrazoline ethyl-sulphate of melting point 188°–190° C.; and 1[4-(3-trimethylammonium)-propylsulphonylphenyl]-3-(4,5-dichloro-2-methylphenyl)-pyrazoline p-toluene-sulphonate of melting point 187°–188° C.

EXAMPLE 4

Polyacrylonitrile textile fabric is treated at the boil, in a liquor ratio of 1:40 for 30 minutes with a dye liquor which contains 0.3% of the whitener obtained according to Example 1 and 3% of 30% strength acetic acid (both relative to the textile material). After rinsing and drying, a polyacrylonitrile fabric which has been brightened very well and brilliantly is obtained.

Wool can be correspondingly brightened very well by customary dyeing processes (liquor ratio 1:40, 60 minutes at 55° C. and addition of 3 g/l of a commercially available wool-bleaching agent). The remaining quaternised compounds described in Examples 1 to 3 likewise give good brightening effects on polyacrylonitrile fabric and wool by the processes indicated above.

We claim:

1. A pyrazoline compound selected from the group consisting of

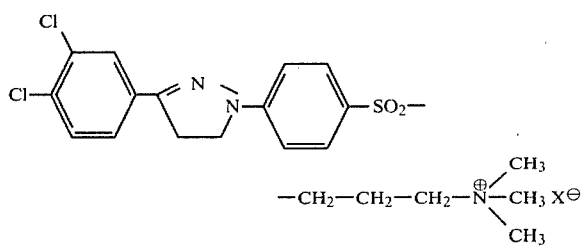

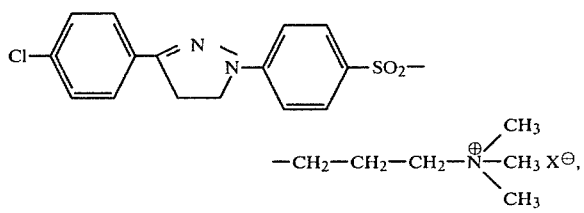

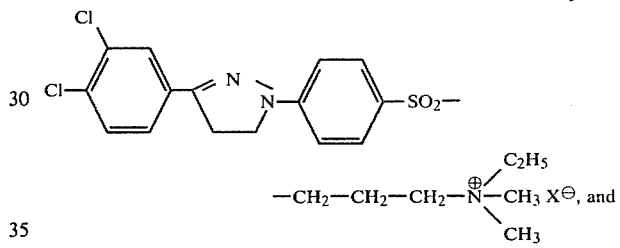

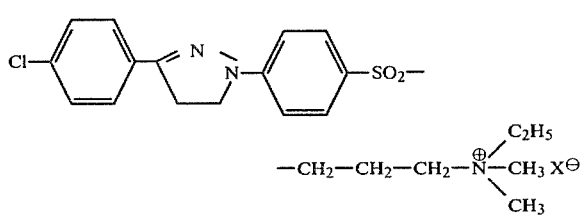

wherein $X^\ominus$ is a colorless anion.

2. A compound according to claim 1 of the formula

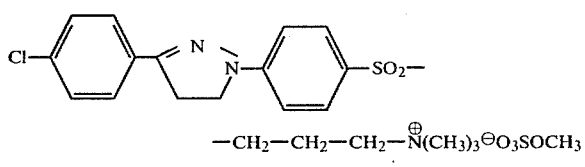

* * * * *